US009983174B2

United States Patent
Bentouhami

(10) Patent No.: US 9,983,174 B2
(45) Date of Patent: May 29, 2018

(54) METHOD AND SYSTEM TO VERIFY THE CALIBRATION OF A SYSTEM FOR NON-DESTRUCTIVE TESTING

(71) Applicant: AIRBUS OPERATIONS (S.A.S.), Toulouse (FR)

(72) Inventor: Franck Bentouhami, Chavagnes en Paillers (FR)

(73) Assignee: Airbus Operations (S.A.S.), Toulouse (FR)

( * ) Notice: Subject to any disclaimer, the term of this patent is extended or adjusted under 35 U.S.C. 154(b) by 338 days.

(21) Appl. No.: 14/883,374

(22) Filed: Oct. 14, 2015

(65) Prior Publication Data

US 2016/0109409 A1  Apr. 21, 2016

(30) Foreign Application Priority Data

Oct. 15, 2014  (FR) ...................... 14 59875

(51) Int. Cl.
*G01N 29/24* (2006.01)
*G01N 29/04* (2006.01)
*G01N 29/30* (2006.01)
*G01N 29/44* (2006.01)

(52) U.S. Cl.
CPC ............. *G01N 29/04* (2013.01); *G01N 29/24* (2013.01); *G01N 29/30* (2013.01); *G01N 29/44* (2013.01); *G01N 29/4427* (2013.01); *G01N 2291/2694* (2013.01)

(58) Field of Classification Search
CPC .............. G01N 29/44; G01N 29/4409; G01N 29/4427; G01N 29/4436; G01N 29/4445; G01N 29/4454; G01N 29/4463; G01N 29/4472; G01N 29/4481; G01N 29/449; G01N 29/46; G01N 29/48; G01N 29/50; G01N 29/52

See application file for complete search history.

(56) References Cited

U.S. PATENT DOCUMENTS 3,677,061 A * 7/1972 Visser .................... G01N 29/30
                                                         73/1.83
3,908,439 A * 9/1975 Pelak .................... G01M 3/007
                                                         73/1.86

(Continued)

OTHER PUBLICATIONS

Search Report cited in French Patent Application No. 1459875 dated Jul. 15, 2015, 2 pages.

(Continued)

*Primary Examiner* — Peter Macchiarolo
*Assistant Examiner* — Alexander Mercado
(74) *Attorney, Agent, or Firm* — Nixon & Vanderhye P.C.

(57) ABSTRACT

A method and assembly for verification of the calibration of a system for non-destructive testing of pieces. The assembly includes an ultrasound probe, a perfect reflector having reference defects, and recording and data processing units. The ultrasound probe scans the perfect reflector and ultrasonic reflections from the reflector are measured by the non-destructive testing system, a recording unit records the measurements, and a data processing unit forms a virtual map of the perfect reflector based on the amplitude and time of flight of the reflections and based on predetermined characteristics of the material of the reflector.

11 Claims, 2 Drawing Sheets

(56) References Cited

U.S. PATENT DOCUMENTS

| | | | | |
|---|---|---|---|---|
| 4,068,524 A * | 1/1978 | Lewis | G01N 29/40 | 73/611 |
| 4,173,139 A * | 11/1979 | Conn | G01N 29/4463 | 73/1.84 |
| 4,203,315 A * | 5/1980 | Vieu | G01N 29/30 | 73/1.86 |
| 4,453,408 A * | 6/1984 | Clayman | G01H 3/005 | 73/1.86 |
| 4,466,270 A * | 8/1984 | Kimura | G01N 29/30 | 73/1.86 |
| 4,558,585 A * | 12/1985 | Berry, Jr. | G01N 29/30 | 72/324 |
| 4,660,419 A * | 4/1987 | Derkacs | G01N 29/30 | 250/252.1 |
| 4,704,892 A * | 11/1987 | Tarnai | G01N 29/30 | 29/428 |
| 4,729,235 A * | 3/1988 | Podlech | G01N 29/30 | 73/1.86 |
| 4,747,295 A * | 5/1988 | Feist | G01N 29/30 | 29/407.07 |
| 4,903,523 A * | 2/1990 | Flynn | G01D 18/00 | 600/437 |
| 5,054,310 A * | 10/1991 | Flynn | G01D 18/00 | 73/1.86 |
| 5,062,297 A * | 11/1991 | Hashimoto | G01B 17/06 | 73/597 |
| 5,163,027 A * | 11/1992 | Miller | G01B 3/30 | 367/13 |
| 5,700,955 A * | 12/1997 | Roth | G01B 17/06 | 702/142 |
| 5,837,880 A * | 11/1998 | Shakinovsky | G01N 29/223 | 73/1.86 |
| 6,415,644 B1 * | 7/2002 | Rockwood | G01B 17/02 | 73/1.86 |
| 7,194,908 B2 * | 3/2007 | Nenno | G01N 29/0609 | 73/618 |
| 7,216,544 B2 * | 5/2007 | Vaccaro | G01N 29/11 | 204/192.13 |
| 7,464,579 B2 * | 12/2008 | Orchard | G01B 3/30 | 73/1.81 |
| 7,617,715 B2 * | 11/2009 | Georgeson | G01N 29/11 | 29/593 |
| 7,694,546 B2 * | 4/2010 | Engelbart | G01N 29/30 | 73/1.82 |
| 7,694,890 B2 * | 4/2010 | Kudoh | G01S 15/74 | 235/494 |
| 7,701,562 B2 * | 4/2010 | Nemoto | G01B 5/008 | 356/123 |
| 7,743,639 B2 * | 6/2010 | Bamberg | G01N 29/30 | 73/1.86 |
| 7,752,882 B2 * | 7/2010 | Vaccaro | G01N 29/30 | 73/1.82 |
| 7,762,120 B2 * | 7/2010 | Vaccaro | G01N 29/30 | 73/1.86 |
| 2007/0000328 A1 | 1/2007 | Buttram | | |
| 2008/0006091 A1 * | 1/2008 | McKeon | G01N 29/043 | 73/627 |
| 2011/0274369 A1 * | 11/2011 | Smith | G01N 29/069 | 382/280 |
| 2014/0047934 A1 * | 2/2014 | Dominguez | G01N 29/043 | 73/866.4 |
| 2016/0209375 A1 * | 7/2016 | Yamaoka | G01N 29/04 | |
| 2017/0082582 A1 * | 3/2017 | Fendt | G01N 29/0672 | |

OTHER PUBLICATIONS

Reverdy, F. et al., "Simulation of Ultrasonic Inspection for Sodium Cooled Reactors Using CIVA," 2011 2nd International Conference on Advancements in Nuclear Instrumentation Measurement Methods and their Applications (ANIMMA), IEEE, Jun. 6, 2011, pp. 1-8.

Rebello, Joao Marcos A. et al., "Simulation-Aided UT Weld Inspection for Improving Integrity During Pipe Manufacture," 2014 IEEE Far East Forum on Nondestructive Evaluation/Testing, IEEE, Jun. 20, 2014, pp. 5-8.

\* cited by examiner

METHOD AND SYSTEM TO VERIFY THE CALIBRATION OF A SYSTEM FOR NON-DESTRUCTIVE TESTING

RELATED APPLICATION

This application claims priority to French patent application 1459875, filed Oct. 15, 2014.

FIELD OF THE INVENTION

The present invention relates to a method of verification of the calibration of a system for non-destructive testing of at least one piece, such as a piece of an aircraft. In particular the invention relates to a non-destructive testing system using an ultrasound probe to detect defects inside of a piece, such as a piece made of a composite material.

BACKGROUND OF THE INVENTION

Ultrasound testing is usually based on the transmission and the reflection of ultrasound waves within the material of the piece to be tested, and the analysis of the echoes detected in combination with the waves emitted.

Generally speaking, the verification of the calibration of such a non-destructive testing system, prior to the testing of a piece, is carried out with the aid of a reference (or standard) piece which is fabricated using the same material and with the same process as the piece to be tested.

Such reference pieces are gauge blocks whose geometry is known, controlled and regularly checked. They have, in general, various thicknesses in order to be able to create an amplitude-distance correction of the CAD type, and holes with a flat bottom in order to verify the detection.

Generally speaking, the reference pieces are used to carry out:

(i) a verification prior to each scanning of the ultrasound configuration (namely of an amplitude-distance correction);

(ii) a verification of detection minima. These characteristics may be influenced by the ultrasound properties, such as the frequency, the shape of the acoustic beam, the bandwidth, and the scanning means mechanics of the non-destructive testing system; and (iii) a verification to ensure that the non-destructive testing system exhibits a behavior which can be repeated over time (by comparing mappings of the same reference piece over time).

However, this method of verification of the calibration of the non-destructive testing system has a drawback associated with the necessity to use such reference pieces. Indeed, the reference pieces are very costly. Moreover, their use in the verification of the calibration requires:

(i) the fabrication of many reference pieces;
(ii) their periodic validation; and
(iii) the fabrication of new reference pieces notably in the case of wear or of damage.

SUMMARY OF THE INVENTION

The present invention relates to a method of verification of the calibration of a system for non-destructive testing of at least one piece, allowing this drawback to be overcome.

A method and system have been invented and are disclosed herein for the verification of the calibration of a system for non-destructive testing of at least one piece using at least one ultrasound probe. The method, in one embodiment, may include successive steps E1 to E3 of:

E1—carrying out measurements, by means of the non-destructive testing system, on at least one reflector said to be perfect, said perfect reflector comprising at least one reference defect, in recording the measurements thus performed, and in creating and analyzing an ultrasound mapping of an entry surface of the perfect reflector;

E2—determining a virtual probe, based on physical data of the ultrasound probe, associating it with a bandwidth representative of measurements carried out at the step E1; and E3—determining a virtual gauge block and a virtual mapping (also referred to as a virtual map) in amplitude and in time of flight of a bottom surface of the virtual gauge block, by means of a modeling using, as input data for the characteristics of the piece, the virtual probe determined at the step E2 and measurements carried out at the step E1, and in analyzing said virtual mapping in order to deduce characteristics of the calibration of said non-destructive testing system.

The verification of the calibration may be carried out with the aid of a perfect reflector exhibiting reference defects, which is used in combination with characteristics of the material of the piece, via a modeling. It is thus not necessary, as described below, to provide one reference piece per type of material and per type of piece fabrication process, which allows the aforementioned drawback to be overcome.

The method may include an additional step E0 prior to the step E1. The additional step E0 includes determining the characteristics of a material corresponding to that of the piece to be tested, allowing a virtual reference piece, used at the step E3, to be defined.

The method may further include in providing on the perfect standard at least one reference defect chosen from amongst: a hole with a flat bottom; a through hole; a machined piece edge; a defect-free area; and a bead.

Furthermore, the method of verification of the calibration may include one or more of the following features:

(i) the analysis at the step E1 of the ultrasound mapping of the entry surface consists in verifying mechanical means, e.g., the mechanical components, for the non-destructive testing system;

(ii) at the step E3, the analysis of the virtual mapping of the bottom surface consists in verifying whether reference defects of the perfect reflector are present on this virtual mapping and have been detected and in comparing the amplitude of the virtual mapping with a predetermined value;

(iii) the step E1 is carried out with an ultrasound probe in an initial state and a virtual mapping is generated at the step E3;

Further, the method may include at least one step for storing at least some of the following information: measurements recorded at the step E1; at least one mapping; and properties of the ultrasound probe.

The present invention also relates to a method for testing a piece, by means of a non-destructive testing system comprising at least one ultrasound probe, said testing method comprising a method of verification of the calibration of the non-destructive testing system, such as that aforementioned.

The present invention furthermore relates to an assembly for verification of the calibration of a non-destructive testing system, for the implementation of the aforementioned method.

The assembly may comprise: at least one perfect reflector, comprising at least one reference defect and on which measurements are performed by means of the non-destructive testing system; a recording unit configured for recording the measurements carried out on said perfect reflector; and a data processing unit configured for determining at least one virtual mapping in amplitude and in time of flight by means of a modeling, based on values measured and received from said recording unit. The at least one reference defect of the perfect standard may be selected from: a hole with a flat bottom; a through hole; a machined piece edge; a defect-free area; and a bead.

SUMMARY OF THE DRAWINGS

The appended figures will allow it to be well understood how the invention may be implemented. In these figures, identical references denote similar elements.

DETAILED DESCRIPTION OF THE INVENTION

Figure 1:
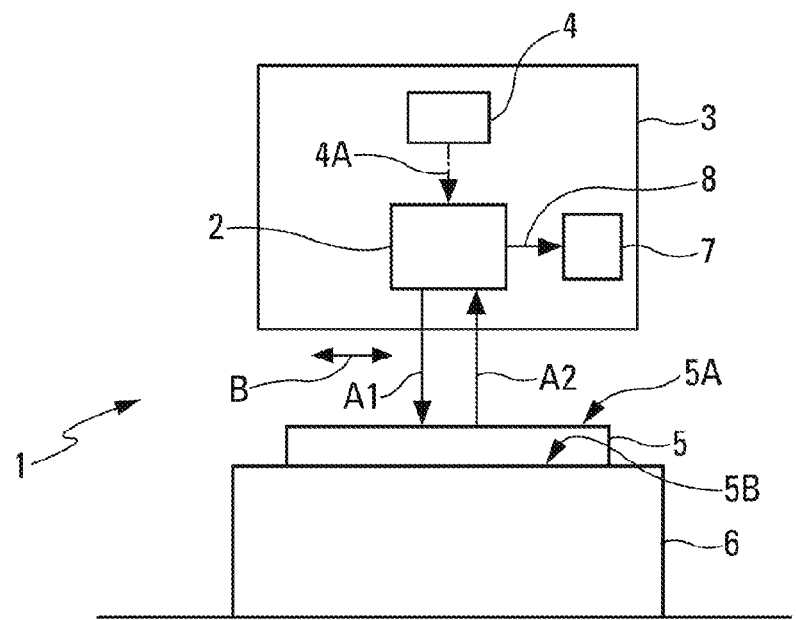
FIG. 1 is a schematic diagram of one example of non-destructive testing system, to which the invention is applicable.

FIG. 1 shows a system 1 for the non-destructive testing of at least one piece 5. With regard to the piece, this may, for example, be a panel of a fuselage of an aircraft, in particular of a transport plane. The present invention is described, by way of example, for a piece 5 made of composite material, but may also be applied to any type of material.

As shown schematically in FIG. 1, a testing system 1 of the non-destructive type comprises at least one ultrasound probe 2, installed on a mechanical assembly 3. The ultrasound probe 2 emits waves in the form of an acoustic beam whose frequency is situated within the ultrasound range of frequencies (between 16,000 and 10,000,000 Hertz). The mechanical assembly 3 comprises conventional devices 4 (such as an emission source, a robot, a support structure) for generating a scanning of the ultrasound probe 2 over a piece 5 positioned on a support 6 and for adjusting its position, as illustrated by an arrow 4A. In the example described hereinbelow, the ultrasound probe 2 follows a scanning path parallel to a surface of the piece 5.

The ultrasound probe 2 is usually characterized by various physical properties such as the frequency, the shape, the focal length or the bandwidth of the acoustic beam.

The testing system 1 allows a non-destructive testing of a piece 5 (for example made of material composite), notably a piece of an aircraft, to be carried out in order to detect defects in the piece 5.

Ultrasound non-destructive testing may comprise:

(i) the emission of ultrasound waves by the probe 2 toward the piece 5 to be tested, as illustrated schematically by an arrow A1 in FIG. 1. The ultrasound waves penetrate into the piece 5 via a first face of the piece 5, called entry surface 5A, and pass though the piece 5 up to a second face of the piece 5, called bottom surface 5B;

(ii) the reflection of the ultrasound waves by the piece 5 and the detection of the ultrasound reflected waves by the piece 5 (as illustrated by an arrow A2). These ultrasound waves are reflected by the entry surface 5A (entry ultrasonograph), by the bottom surface 5B and by various elements, such as defects, situated between the entry surface 5A and the bottom surface 5B (bottom ultrasonograph);

(iii) the generation and the analysis of a mapping of the amplitude of the reflected waves and time of flight of the reflected ultrasound waves provides data representative of the thickness of the piece 5, and of the depth and location of features in the piece.

Figure 3:
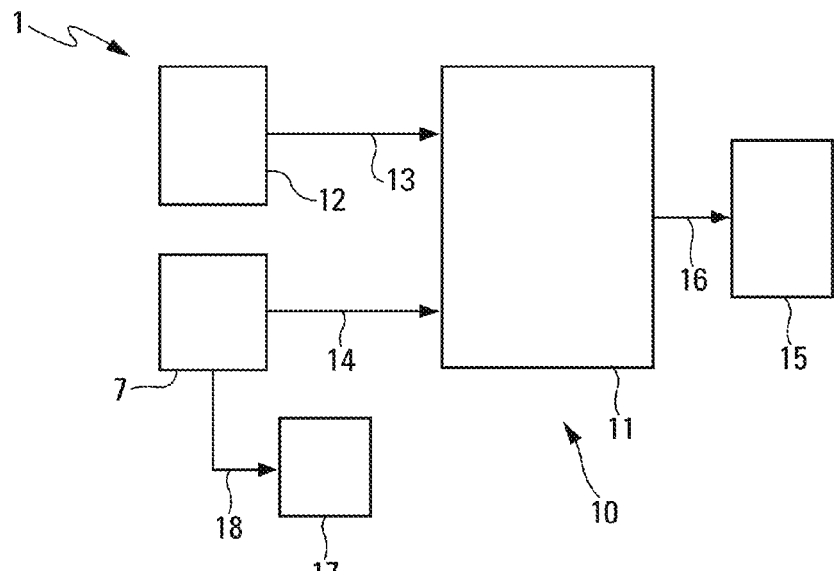
FIG. 3 illustrates a verification assembly for implementing at least one calibration verification.

The testing system 1 comprises an assembly 10, as shown in FIG. 3 may include:

(i) a data processing unit 11 comprising data processing software (such as the application CIVA® published by the company CEA LIST) configured for modeling a mapping of the reflected ultrasound waves based on characteristics and properties of the material of the piece 5, such as the type of composite material (nature of the resin, type of fiber, drape forming sequence, density by volume of fibers) and ultrasound characteristics of the acquisition system (which are measured on a perfect reflector as described hereinbelow);

(ii) a man-machine interface unit 12, for example a screen/keyboard assembly, allowing an operator to input data into the data processing unit 11 via a link 13 notably;

(iii) a recording unit 7 including non-transitory memory for recording the measurements carried out by the ultrasound probe 2 and received via a link 8 (FIG. 1) and supplying the data recorded to the data processing unit 11, either directly (for example via a link 14), or indirectly via the man-machine interface unit 12; and (iv) a presentation unit for presenting the data 15, for example a display or printer unit, which receives the results of the processing operations implemented by the data processing unit 11 via a link 16 and displays them to an operator.

Figure 2:
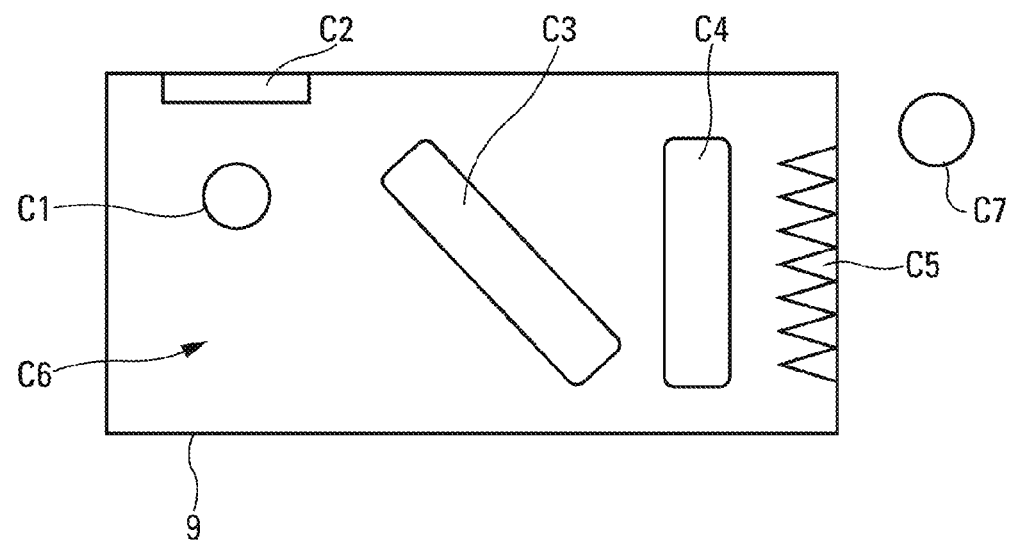
FIG. 2 is a schematic plan view of one example of a perfect reflector, able to be used for the implementation of the invention.

In order to carry out a verification of the calibration of the testing system 1, a reflector, referred to as a perfect reflector 9 (or standard reflector), is used and is shown by way of illustration in FIG. 2. This perfect reflector 9 contains reference defects C1 to C5 formed by machining (through-hole or otherwise) whose dimensional characteristics are known, together with areas without defects such as the area C6.

In one particular embodiment, the perfect reflector 9 takes the general form of a rectangular plate, made of a material such as glass or metal. It comprises reference defects C1 to C5, such as:

(i) a hole with a flat bottom C1 (or through-hole), for example 6 mm in diameter;

(iii) a machining C2 of the edge of the plate (going through or otherwise), for example with a width of 6 mm;

(iv) a machining C3, C4 on the plate, for example with a width of 6 mm; and (iv) a characteristic end machining C5 (for example with a toothed or comb shape).

Advantageously, the perfect reflector 9 can also comprise a bead C7.

Figure 4:
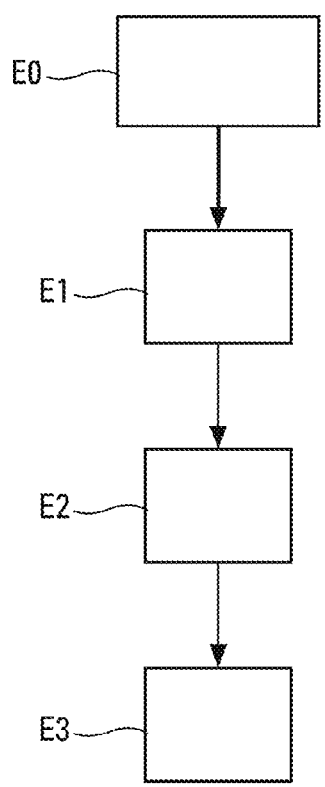
FIGS. 4 and 5 are schematic flow diagrams, respectively, of a calibration verification method and of a method for non-destructive testing of a piece.

The verification of the calibration of the testing system 1 is implemented, prior to the effective testing of the piece 5, by means of the assembly 10. This verification comprises a series of steps E0, and E1 to E3 (FIG. 4) such as:

E0: obtaining and archiving of the characteristics and properties of a material corresponding to that of the piece 5;

E1: inspection of the perfect reflector 9, generation and analysis of an ultrasound mapping of the entry surface of the perfect reflector 9, referred to as entry physical mapping;

E2: creation, in the data processing unit 11, of a probe, referred to as virtual probe, based on physical data of the ultrasound probe 2, such as the dimensions, the geometry, and other parameters, associating the virtual probe with a bandwidth, representative of the measurements carried out at the step E1; and E3: modeling, by the data processing unit 11, of a virtual gauge block and mapping in amplitude and in time of flight of the bottom surface of the virtual gauge block, referred to as virtual base mapping.

The step E0 is a step that may be implemented prior to the effective verification of the calibration. This step E0 allows to obtain and to archive characteristics and properties of the material of the piece 5 to be tested later on, notably in the form of a matrix of coefficients Cij. The coefficients Cij relate to a constant of elasticity and correspond to the various values of a matrix used for mathematically re-transcribing the mechanical behavior of the material.

This step E0 may be implemented on a characterization test bench or by means of an inverse method (starting from real ultrasound data obtained on a single reference piece per material and per process). Step E0 is implemented once. The characteristics of the material of the piece 5 may be obtained in a centralized manner in a specific site or laboratory which archives them and subsequently supplies them to the various users carrying out non-destructive testing processes by means of a testing system 1.

This step E0 allows a virtual reference piece to be defined in the data processing unit 11 whose material properties and characteristics, namely for a composite material, nature of the fibers, type of resin, drape forming sequence and fiber density by volume are known and can be used as input parameters.

The step E0 thus allows:

(i) the characteristics and properties of the material and the matrix of the coefficients Cij to be obtained and archived, these operations being carried out only once for a given material and the results being re-used every time a verification of the calibration for testing a piece 5, composed of said given material, is implemented; and (ii) the creation of a virtual reference piece, recorded in the data processing unit 11.

Furthermore, the steps E1 to E3 are carried out in the framework of a non-destructive testing of a piece 5.

The step E1 includes measuring and recording the measurements of an inspection of the perfect reflector 9, by scanning the ultrasound probe 2 over the perfect reflector 9, positioned on the support 6. The signals from the entry ultrasonograph (conventionally called "A-Scan" signals) at each point of the entry surface are processed by the data processing unit 11 (and notably the data processing software), which generates (or creates) a mapping of the entry surface of the perfect reflector 9, called entry physical mapping.

The analysis of the entry physical mapping consists in identifying, where they exist, one or more areas of the entry surface not having been (or only partially) scanned by the beam of ultrasound waves owing to a mechanical fault in the means 4, such as the system for emission or for scanning of the beam (shift of an axis for example) of the ultrasound probe 2. The analysis of the "A-Scan" signals from the area C6 supplies information on the frequency content of the probe 2. Advantageously, the analysis of the entry physical mapping of the bead C7 validates the physical properties of the ultrasound probe 2 and allows any potential mechanical anomalies to be identified in the system for focusing the beam of ultrasound waves emitted by the ultrasound probe 2.

In the step E2, a virtual probe is generated in the data processing unit 11 and, more particularly, in the data processing software. This virtual probe has the same physical characteristics (dimensions, geometry of the various mechanical elements and identification of the activated elements in the case of a multi-element probe) as the ultrasound probe 2. Advantageously, the generated virtual probe is archived in the data processing unit 11, and this step E2 is only carried out when the ultrasound probe 2 is replaced or when it is desired to compare the state of the ultrasound probe at a given moment in time with respect to a preceding state.

A value of bandwidth (and of central frequency where necessary) of the virtual probe thus created is determined in the data processing software at each calibration. The input value corresponds to the value of the bandwidth of the measurements carried out at the step E1. During the step E3, the data processing software models a virtual gauge block representing a piece made of the material of the piece 5 comprising the reference defects of the perfect reflector 9 (this virtual gauge block corresponds to a gauge block conventionally used in the prior art). For this purpose, the data processing software uses:

(i) the characteristics of the material of the piece 5 obtained at the step E0;

(ii) the measurements carried out and recorded at the step E1; and (iii) the virtual probe generated at the step E2.

The software subsequently generates a virtual mapping in amplitude and in time of flight of the bottom surface of the virtual gauge block, called virtual base mapping. The analysis of the virtual base mapping (also referred to as virtual mapping of the bottom echography) verifies that the various reference defects of the perfect reflector 9 are present on this mapping and have therefore been detected (during the measurement in E1 and during the modeling). If necessary, the dimensional characteristics of the defects present on the virtual mapping (of the echography) of the bottom are measured and compared with the known dimensional characteristics of the reference defects of the perfect reflector. Furthermore, the amplitude of the virtual base mapping is compared with the expected value (for example 80%) and its uniformity is checked.

In one variant embodiment of the verification of the calibration, the step E1 is carried out when the ultrasound probe 2 is in its initial state, for example after purchase, installation and adjustment on the non-destructive testing system 1. In this variant, the measurements carried out on the perfect reflector 9 are used during the step E3 and will allow an initial virtual base mapping to be generated, which will be able to be used as reference during later calibrations.

The usual calibration is thus replaced by a method based on a modeling and the scanning of a perfect reflector 9 exhibiting standard (or reference) defects, for acquiring and verifying the quality of the measurement (uniformity of the amplitude) and the mechanical behavior of the ultrasound probe 2 and of the mechanical assembly 3. The perfect reflector 9 is more stable over time and less costly to produce. Moreover, the characteristics and properties of the material of the piece 5 are stored in the data processing unit 11 (or in a storage unit 17 described herein below) and re-used at each calibration. Thus, this solution allows the systematic need for a standard piece (or gauge block), formed with the same material and process as the piece 5 to be tested, to be largely obviated.

Depending on results of the verification of the calibration, implemented by means of the verification assembly 10, various actions may be envisioned. By way of illustration:

(i) if the calibration falls within predefined acceptable limits, the probe 2 and the testing system 1 are considered as compliant for the testing of the piece 5;

(ii) if a slight calibration defect is observed, with small variations, a software compensation of the measurements can be applied;

(iii) if the calibration defect remains limited, it may also be envisioned for a correction of the mechanical adjustment of the probe 2 to be carried out; and (iv) if a significant calibration defect is detected, the probe 2 may be replaced by another probe, and subsequently the calibration of this new probe verified.

In one particular embodiment, the assembly 10 also comprises, as shown in FIG. 3, the storage unit 17 for storing the various data from the verification of the calibration of the ultrasound probe 2 received from the recording unit 7 via a link 18, such as the properties of the probe 2, the parameters of the measurements performed and the mappings generated. This storage unit 17, which includes a non-transitory electronic memory, thus allows any potential variations of the testing system 1 over time to be evaluated and characterized.

Figure 5:
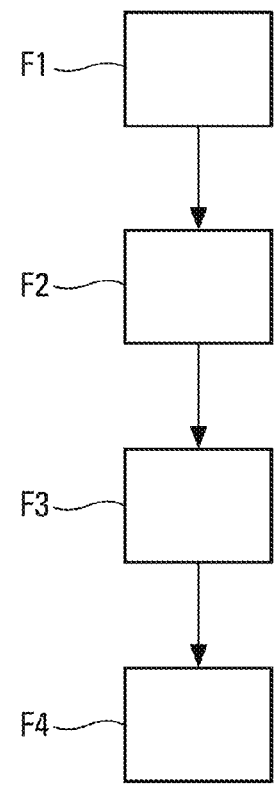

The method for non-destructive testing of a piece 5, implementation by means of the testing system 1, comprises the following successive steps F1 to F4, shown in FIG. 5:

F1 preparation of the test, including: cleaning the piece 5 (such as scouring to optimize the wettability of the piece), and arranging the elements of the testing system 1;

F2 verification of the calibration of the ultrasound probe 2, such as described hereinabove and notably comprising the aforementioned steps E1 to E3;

F3 inspection and analysis of the piece 5, identical to the inspections and analyses conventionally carried out, with a scanning of the piece 5 and recording of the bottom ultrasonograph, and potentially of the entry ultrasonograph, by means of the recording unit 7.

An analysis is performed of the mappings of the piece 5 in amplitude, in order to verify that the amplitude is uniform and has the desired value (for example 80%); an analysis is also performed of the mappings of the piece 5 in time of flight, so as to verify the presence or the absence of defects; and F4 is an end-of-test step comprising removal of the piece 5 from the testing system 1; and where necessary, dismantling of the elements of the testing system 1.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention is:

1. A method of verification of the calibration of a system for non-destructive testing of at least one piece, said system for non-destructive testing comprises at least one ultrasound probe, and the method includes successive steps E1 to E3 which comprise:

E1—carrying out measurements, by means of the non-destructive testing system, on at least one standard reflector including at least one reference defect, recording the measurements, and creating and analyzing an ultrasound mapping of an entry surface of the standard reflector;

E2—determining a virtual probe based on physical data of the at least one ultrasound probe, and associating the virtual probe with a bandwidth representative of measurements carried out at the step E1; and E3—modeling a virtual gauge block and creating a virtual mapping in amplitude and in time of flight of a bottom surface of the virtual gauge block using characteristics of the at least one piece, the virtual probe and measurements carried out in the step E1 as input data, and analyzing said virtual mapping to deduce dimensional characteristics of the virtual mapping and comparing the dimensional characteristics of the virtual mapping to known dimensional characteristics of standard reflector to determine calibration of said non-destructive testing system.

2. The method according to claim 1, further comprising determining a characteristic of a material of the at least one piece to be tested and using the characteristic to define a virtual reference piece.

3. The method of claim 1, wherein step E1 includes verifying the at least one ultrasound probe.

4. The method of claim 1 wherein the analysis of the virtual mapping in step E3 includes analysis of the virtual mapping of the bottom surface to verify whether reference defects of the standard reflector are in virtual mapping and to compare the amplitude of the virtual mapping with a predetermined amplitude value.

5. The method of claim 1 wherein the standard reflector includes at least one reference defect that is at least one of: a hole with a flat bottom; a through hole; a machined piece edge; and a bead.

6. The method of claim 1 further comprising storing at least one of the following information: measurements recorded at the step E1; the virtual mapping, and properties of the ultrasound probe.

7. A method for testing a piece, comprising
performing the method for verification of the calibration of the non-destructive testing system according to claim 1; and
testing the piece with the non-destructive testing system.

8. An assembly for verification of a calibration of a non-destructive testing system comprising:
at least one standard reflector comprising at least one reference area, and on which measurements are to be performed by means of the non-destructive testing system;
a recording unit configured for recording the measurements carried out on said standard reflector; and
a data processing unit configured to determine at least one virtual mapping in amplitude and in time of flight by modeling, based on values measured and received from said recording unit, and configured to determine at least one dimensional characteristic of the virtual mapping and compare the dimensional characteristics of the virtual mapping to known dimensional characteristics of standard reflector to determine calibration of said non-destructive testing system.

9. The assembly according to claim 8, wherein said at least one reference defect area of the standard reflector includes at least one of:
a hole with a flat bottom;

a through hole;
a machined piece edge;
a defect-free area, and
a bead.

10. A method of verification of a calibration of a system for non-destructive testing of at least one piece, wherein the system for non-destructive testing includes at least one ultrasound probe, and the method comprises:

E1—measuring, using the non-destructive testing system, at least one standard reflector including at least one reference defect, recording the measurements of the standard reflector, and creating and analyzing an ultrasound map of an entry surface of the standard reflector;

E2—determining a virtual probe, based on physical data of the ultrasound probe, and associating the virtual probe with a bandwidth representative of the measuring in step E1, and E3—modeling a virtual gauge block and creating a virtual mapping of amplitude and time of flight with respect to a bottom surface of the virtual gauge block, using as inputs data characteristics of the at least one piece, and using the virtual probe and using the measurements taken the step E1, and analyzing said virtual mapping to determine at least one dimensional characteristic of the virtual mapping and comparing the dimensional characteristics of the virtual mapping to known dimensional characteristics of standard reflector to determine calibration of said non-destructive testing system.

11. The method of claim 10 wherein step E1 is performed with the ultrasound probe in an initial state and the virtual mapping generated in step E3.

* * * * *